United States Patent
Wei et al.

(10) Patent No.: US 11,155,828 B2
(45) Date of Patent: Oct. 26, 2021

(54) SPECIFIC EXPRESSION PROMOTERS IN RICE AND THE USE THEREOF

(71) Applicant: Rice Research Institute, Anhui Academy of Agricultural Sciences, Anhui (CN)

(72) Inventors: Pengcheng Wei, Hefei (CN); Juan Li, Hefei (CN); Jianbo Yang, Hefei (CN); Hao Li, Hefei (CN); Ruiying Qin, Hefei (CN); Rongfang Xu, Hefei (CN)

(73) Assignee: RICE RESEARCH INSTITUTE, ANHUI ACADEMY OF AGRICULTURAL SCIENCES, Hefei (CN)

( * ) Notice: Subject to any disclaimer, the term of this patent is extended or adjusted under 35 U.S.C. 154(b) by 308 days.

(21) Appl. No.: 16/353,874

(22) Filed: Mar. 14, 2019

(65) Prior Publication Data
US 2020/0010846 A1 Jan. 9, 2020

(30) Foreign Application Priority Data

Jul. 3, 2018 (CN) .......................... 201810716882.X
Jul. 3, 2018 (CN) .......................... 201810719642.5

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8237* (2013.01)

(58) Field of Classification Search
None
See application file for complete search history.

(56) References Cited

FOREIGN PATENT DOCUMENTS

WO    WO-03008540 A2 *  1/2003  ........... C12Q 1/6895

OTHER PUBLICATIONS

Duan et al., "An efficient and high-throughput protocol for Agrobacterium-mediated transformation based on phosphomannose isomerase positive selection in Japonica rice (*Oryza sativa* L.)", Plant Cell Reports, vol. 31, 2012, p. 1611-1624.
Ray et al., "Analysis of transcriptional and upstream regulatory sequence activity of two environmental stress-inducible genes, NBS-Str 1 and BLEC-Str8, of rice", Transgenic Research, vol. 21, 2012, p. 351-366.
Ye et al., "Two novel positive cis-regulatory elements involved in green tissue-specific promoter activity in rice (*Oryza saliva* L ssp.)", Plant Cell Reports, vol. 31, 2012, p. 1159-1172.

* cited by examiner

*Primary Examiner* — Stephen Uyeno
(74) *Attorney, Agent, or Firm* — Birch, Stewart, Kolasch & Birch, LLP

(57) ABSTRACT

The present invention provides the specific expression promoters in rice and the application. The present invention applies the promoter in the plant genetic engineering. The sequence of the promoter provided in the present invention is composed of the nucleotide sequence shown in SEQ ID No. 1; the nucleotide sequence shown in SEQ ID No. 2; Or the nucleotide sequence shown in SEQ ID No. 3.

2 Claims, 7 Drawing Sheets
Specification includes a Sequence Listing.

SEQUENCE LISTING

<160> NUMBER OF SEQ ID NOS: 13

<210> SEQ ID NO 1
<211> LENGTH: 1485
<212> TYPE: DNA
<213> ORGANISM: Oryza sativa

<400> SEQUENCE: 1

| | | | | | |
|---|---|---|---|---|---|
| accccttaa | tcaaaaacaa | caagtgttgg | gacttcagtt | cttttctgag | aagatacctg | 60 |
| gctcgaaggc | tcatcggttc | gctcattggc | accggccgta | tacacggttg | tccctgcccg | 120 |
| tttgagaaat | cgccgtacgg | tggctgaggc | gcttcacgac | agagggtgga | ttaggaacat | 180 |
| caccgccgct | cttggcgtcc | aagctatcct | ggagtatttc | aaactctagg | acatcctcag | 240 |
| atcagttcaa | ctctcggatg | agcctgactc | tctgacttgg | aggtgggagt | cctcaaggga | 300 |
| gtattcttct | cggtcagcat | accgtgctaa | caagagccca | tcttaggcaa | aagttatgtt | 360 |
| cggattaacc | tttaggaacc | gcggaggagc | aacagcgatg | aatgaaacca | accagcgaga | 420 |
| gttgtctacg | acctgccgtc | tggcagaggt | ctcggtaccg | aacagcgtgg | acacgcaac | 480 |
| gcaagaaaca | ctagtttcac | tgctctgata | gctagtggaa | aaccatgcat | gtccagagtc | 540 |
| ttggcagctg | tggtggattg | ctctcagagc | aattgggctt | tcgaaatgct | tgccgatcaa | 600 |
| tgaaccttcc | tttcatcatt | ggctctgtga | tagcaaaaag | aagatgacca | aggcgcatcg | 660 |
| tcggggattt | gacaccatcg | caaccctggt | agcatggacg | atctggaaag | agagaaacaa | 720 |
| tagagttttc | aatcaggtca | gcataacttg | ggtggagatc | gctcgggcca | tgatagacga | 780 |
| agctgatctt | tggaggctgg | ctagggctgc | catacacacc | ttagtagtcc | atgtagatag | 840 |
| agagaggtcg | cttggagatt | aggctctaat | gctcttgcac | ctctcctgta | tcctccccgt | 900 |
| cttgttttc | ttttgttatg | tccacttgta | cataaacttt | atttcttctt | aatataaaga | 960 |
| tgcgctcctt | gcgaattccc | aaaaaaaaca | acaagaagca | agtcatcttc | tttttttttt | 1020 |
| tttttgacg | ctgagcaggt | aatcattaga | acagttagaa | cttttaaaaa | gacaaataat | 1080 |
| gctgctgaaa | atattccacg | aagaataatc | tcatccggcc | aggttccaag | cagccagaac | 1140 |
| ttacttatgc | agaagctagt | catccatggg | tagtatcagt | gtttacactt | ctgagaatcc | 1200 |
| gtatagtaat | tcttctcaga | gtgtgggtgt | ttctcgagct | atgcatctga | taaggaagca | 1260 |
| ttgcatctat | caccaggaaa | accaaataat | tgagctacag | attagttata | ccggtcttac | 1320 |
| tgtccaataa | ttgatttttt | taatggaatc | atagtctcac | agataccacc | aaagccaata | 1380 |
| ctcctccatt | gcctgcatat | aaataacaca | aaagcagacc | ggtcttggca | aaggacactc | 1440 |
| actttgcttt | ctcatactcg | ttggctcgtt | gctcctttgc | atcaa | | 1485 |

<210> SEQ ID NO 2
<211> LENGTH: 1939
<212> TYPE: DNA
<213> ORGANISM: Oryza sativa

<400> SEQUENCE: 2

| | | | | | |
|---|---|---|---|---|---|
| tttactcacc | gtgtcctctg | ttgattttg | tgatgcccaa | attgtttgat | ttcatgatgt | 60 |
| gcttagaact | gttgccagtg | caagttgatt | tacatgtaaa | cctattctat | gatgcatttc | 120 |
| tttcatcctt | catgtgtgaa | tctgtgagat | gaatgcaact | acaactagca | aaagaacatt | 180 |
| tttttcacag | gtaaccagca | gcattgatgg | gccgcattgt | gctactcgtc | acatgtaact | 240 |
| cacttgtgac | gggttgtgac | gcgacaagtt | aaaaggggg | taacattacc | tgtgacgggt | 300 |
| tgtcatttgt | aatctgtcag | aggtgattca | tactagtgac | gtgcctttag | ccgtcaaaga | 360 |

-continued

| | |
|---|---|
| taagtttagt catcactaac cactcatctc ttaccaacgc cctacccgtt agaggtgaca | 420 |
| gtttgagcct gtcaccgatg acccaatcta gtgtaatgat tctcaatatc aaaattgtat | 480 |
| aactcgacga ggtcaaccat tctagatttg atgactattc ttttgatgtc actagcaaaa | 540 |
| tgcccatgcg ttgcaccggg taatgtcgcg ttggataaag tttaactgaa cgatttttta | 600 |
| agcggtatag tatgacaata atagtgatca agtaatcgtt cataattttc tagcaatttt | 660 |
| aaaatggctc aaaataatgc caagaaaatt ttgtaaacga ctaaataaat taaatcgatg | 720 |
| gaattaaata aaattctatt tcgacctatt acttttgtaa ctgacccaaa aaatcggatc | 780 |
| ggcccgttta gcgcgagccg attgcactac aagtggccca tctaccggcg acggcccgac | 840 |
| acgcggcaaa gggcacgcgg ctcagttgtc ttccatggcc caaagactgc acggcccaat | 900 |
| agcggtggcg gcccgatgcg gggccgatct gacccatccg atctgatgga cagcttggat | 960 |
| tggtcccgcg ccaatgaaat cgccggccgg aaggggaggg tccgaaaacc ctaaccctaa | 1020 |
| ttgcctttct tccctactct ccctgatcca atctctggcg acgcgagaga gtggacggcg | 1080 |
| atgatctagt cttctccgc gtctttccgt cttccacccg agttgtcgcc gactagatca | 1140 |
| tccaccggct ccaagccgtc attcatgctc gtgtggatcc gccgtcggcg cctagatccc | 1200 |
| atcgtctctc ggcgatagcc gcatggcagc tgcgatggcc aaggcgcgtg gcagcagcg | 1260 |
| agactggtgg gcgcggatc tgccggctgg ggaggcttga gggcgcggag gtggctgagt | 1320 |
| tttggcagcc gcctcacaaa gttgccgcca ccgcctgctt cctcgacatc gccactagcg | 1380 |
| ggagatgtta acaaggctaa catgtaacgt atgagcccca aatttgaatc ctatatgcta | 1440 |
| catgtgtgaa aatttgtgtg tagatgtata gtaaaatgtg aacttttttt tatggttttt | 1500 |
| tcacctataa aaataaaaat tggaaaatta ttttcttggt tggtttctta agagagccgt | 1560 |
| gtatgaaaat gagatcatca caagagtttt gttaagagga ccgccaaatg gttctctcct | 1620 |
| tgccgctcga tgcatgtgga aatagttgtt tttctacagg ttacagctta caagtgacat | 1680 |
| aacggtttga taaacgactg tagccaaaag tacttttcaa tcactttaat tttggtcagc | 1740 |
| tcccgtacat gtagttaact tgatctttgc acgcaagcaa ttattttct gtcaccacgc | 1800 |
| tcctcgacga cctctgcata cggctataaa atcacatgca acccctcaat aaccaaagca | 1860 |
| tcttactcaa agtctcaaac gataaccaca gggagaggag ctagtaaaaa tagctagcta | 1920 |
| actaccagag agagataca | 1939 |

<210> SEQ ID NO 3
<211> LENGTH: 2072
<212> TYPE: DNA
<213> ORGANISM: Oryza sativa

<400> SEQUENCE: 3

| | |
|---|---|
| aatctctact acttaaattc cataattta gaaagggtga aaaaaaatca tgcgggaaaa | 60 |
| gaaaacgcat cgtaatgaaa cgcgaaagaa aaacagcgaa aaaagtccg atccggactg | 120 |
| gaaacgggaa aaataatgtg gcggaaaaaa gctgaaaaaa acagaaaaag ccgactgtac | 180 |
| aaaaatataa aagtcgccga tcgtaaaaaa aataagaaa gccacgcgaa actgtcgtct | 240 |
| aaaaaacggt gtagaaaaaa gaccgtaaaa attaccagag aaaaaaacac attataaaac | 300 |
| agcaaaaaaa agtccctctc ttttatccgc ctttttttc ttcttttttt ccgcttttat | 360 |
| ttttttccca tccgcttttt tgtccttat atttattcg caattttgt catgagaaag | 420 |
| ggtctgtgca cattgtgagg attctttttt tttatctacc cggttttttc gtcgtcgggc | 480 |

| | |
|---|---|
| cgaactctag caccaccgcc acatcgatcg gccttctcat gctttccctc ctccaattga | 540 |
| ttgaaaaatc aattctccac tactccatca tcatttttccc cataatttttt tcttttattt | 600 |
| ccgctttaat ttatcagatt caatctctat atttagaagt caccatttat atcctagagt | 660 |
| tttatggatt cgctgcggtt ttgataaaaa cggaaagaaa agatcgagtg aataagagca | 720 |
| ctcaaccaat tttaggagat tgagaaagat tggatcgtat ttgatgggga gtattggttc | 780 |
| tggcatcata ctacacggtc ctatcttcga ggttgaacac ggcagtcgac tatacgagat | 840 |
| aggcctatag ctctacttgt ggtctaggtt caaaagaagt aagccaagta gagagaagta | 900 |
| gcgggttggg ccgagactga ataggaagga agaaaataag ttttttatcca aaccaaaag | 960 |
| gtacaatgta tatcaataca ttttaccaaa atgggcaacg ttgcgtgccc gtaaaaaga | 1020 |
| tcattgtatg attatgattt ttagacctgt atggatacaa gtctaaataa tatgatctta | 1080 |
| tacagtatag gtcaggatct aagctaaaaa acctggttcc ttcatggttt taaccattat | 1140 |
| aagctcgttg gtaattggca gatgagtaac gccaatttttt gatgtaagct ctcacgagca | 1200 |
| tcctcaaccg actctacagt catacaactg tagtagttaa caattattta ttcagaaaaa | 1260 |
| aaccaatttc taaccatatc taaatacgta ttcacaagtt ttttttctag gacagagcca | 1320 |
| cgaagggagt atagctacag agaggtgttt aataaactat acaaggtgcc accaagcaca | 1380 |
| atttattcgg gtgtttgatt attatctaga tgaaccacga agcctatccc tataaaaaaa | 1440 |
| aggaaggtgc atttggtctg aggttgtcgc agccatggcg caagaggtcg cttttggcg | 1500 |
| tcttgcccat attcattgta ctgtgcccta tcgtttagtg ttttttttt gttttttttt | 1560 |
| ttacggaggg agtacatcct gaccgcaagt tggtccactg tcagctacgg cacaccagat | 1620 |
| cccagccgct cgtgtcaaaa ttgcacccgt gcgtctaggt gtccgcgtga tacggggccc | 1680 |
| cacggtccag gccacgaccg ggcaggctcc tctcggcccg gctggcaaca cacgtctcgc | 1740 |
| tgccacccct ggcccaccat cccgcagggc ggcagcatct cctgacccca cactccagtc | 1800 |
| acccgccccg ccctaaaacc cactgcgccg gggcccaccc cgccccgcc tccccgccgc | 1860 |
| cgcaccacgc tgctcctacg cgttcttcgt cgagacggcg acgtgagctc tccaagcgcg | 1920 |
| cgctctcctc cgctataaaa ccaggcgccg cgtggaagct tctctcctct tgctagcccc | 1980 |
| accccctcct cctcgtcgtc gtcgtcgtcg tggtctctcc tgctccggcg aggcgacccc | 2040 |
| acggccgcca aggcgcgggt tagctgattt gg | 2072 |

```
<210> SEQ ID NO 4
<211> LENGTH: 28
<212> TYPE: DNA
<213> ORGANISM: Artificial Sequence
<220> FEATURE:
<223> OTHER INFORMATION: Synthetic: FP

<400> SEQUENCE: 4
```

| | |
|---|---|
| ggatccaccc ccttaatcaa aaacaaca | 28 |

```
<210> SEQ ID NO 5
<211> LENGTH: 28
<212> TYPE: DNA
<213> ORGANISM: Artificial Sequence
<220> FEATURE:
<223> OTHER INFORMATION: Synthetic: RP

<400> SEQUENCE: 5
```

| | |
|---|---|
| gtcgacttga tgcaaaggag caacgagc | 28 |

<210> SEQ ID NO 6
<211> LENGTH: 28
<212> TYPE: DNA
<213> ORGANISM: Artificial Sequence
<220> FEATURE:
<223> OTHER INFORMATION: Synthetic: Forward Primer: EcoRI

<400> SEQUENCE: 6 gaattctttã ctcaccgtgt cctctgtt                                28

<210> SEQ ID NO 7
<211> LENGTH: 28
<212> TYPE: DNA
<213> ORGANISM: Artificial Sequence
<220> FEATURE:
<223> OTHER INFORMATION: Synthetic: Forward Primer: HindIII

<400> SEQUENCE: 7
aagctttgta tctctctctg gtagttag                                28

<210> SEQ ID NO 8
<211> LENGTH: 19
<212> TYPE: DNA
<213> ORGANISM: Artificial Sequence
<220> FEATURE:
<223> OTHER INFORMATION: Synthetic: Actin-FP

<400> SEQUENCE: 8
cctgacggag cgtggttac                                          19

<210> SEQ ID NO 9
<211> LENGTH: 20
<212> TYPE: DNA
<213> ORGANISM: Artificial Sequence
<220> FEATURE:
<223> OTHER INFORMATION: Synthetic: Actin-RP

<400> SEQUENCE: 9
ccagggcgat gtaggaaagc                                         20

<210> SEQ ID NO 10
<211> LENGTH: 26
<212> TYPE: DNA
<213> ORGANISM: Artificial Sequence
<220> FEATURE:
<223> OTHER INFORMATION: Synthetic: Gus-FP

<400> SEQUENCE: 10
tacggcaaag tgtgggtcaa taatca                                  26

<210> SEQ ID NO 11
<211> LENGTH: 23
<212> TYPE: DNA
<213> ORGANISM: Artificial Sequence
<220> FEATURE:
<223> OTHER INFORMATION: Synthetic: Gus-RP

<400> SEQUENCE: 11
caggtgttcg gcgtggtgta gag                                     23

<210> SEQ ID NO 12
<211> LENGTH: 28
<212> TYPE: DNA
<213> ORGANISM: Artificial Sequence
<220> FEATURE:
<223> OTHER INFORMATION: Synthetic: Forward primer

```
<400> SEQUENCE: 12
gaattcaatc tctactactt aaattcca                                    28

<210> SEQ ID NO 13
<211> LENGTH: 28
<212> TYPE: DNA
<213> ORGANISM: Artificial Sequence
<220> FEATURE:
<223> OTHER INFORMATION: Synthetic: Reverse primer

<400> SEQUENCE: 13
ggatccccaa atcagctaac ccgcgcct                                    28
```

SPECIFIC EXPRESSION PROMOTERS IN RICE AND THE USE THEREOF

CROSS REFERENCE TO RELATED APPLICATIONS

This non-provisional application claims the benefit under 35 U.S.C. § 119(a) to Patent Application Nos. 201810716882.X, filed in China on Jul. 3, 2018 and 201810719642.5, filed in China on Jul. 3, 2018, all of which are hereby expressly incorporated by reference into the present application.

FIELD OF THE INVENTION

The present invention relates to the fields of biotechnology and plant genetic engineering technology. Specifically, the present invention relates to the isolation and identification of the specific expression promoters in rice and the application.

BACKGROUND

The growth and development of high level biology is a process of spatial and temporal orderly expression and synergistic effect by different genes. Promoters are a nucleotide sequence on the gene upstream, determining the expression pattern and expression intensity of the downstream genes by interaction with the transcription factors. Therefore, promoter is an important element in gene expression regulation and is called as the "switch" of gene expression. Gene promoters are divided into three types, namely constitutive promoters, tissue-specific promoters and inducible promoters.

Recently, a small number of root-specific promoters in plant have been cloned and applied to researches of gene functions, but the amount is small. Also, the reuse of the same promoter in one vector is easy to cause transgene silencing, and the application of the promoter is often affected by the species difference, causing unsatisfactory effect.

Therefore, it is essential to develop more endogenous root-specific promoters of rice and other promoters, providing promoter reserve for plant genetics, improvement and application. Additionally, it is essential to obtain more other types of promoters.

SUMMARY OF THE INVENTION

In one aspect, the present invention provides specific expression promoter in rice, wherein the specific expression promoter is composed of one of the following sequences:

Nucleotide sequence shown in SEQ ID No. 1;
Nucleotide sequence shown in SEQ ID No. 2; and
Nucleotide sequence shown in SEQ ID No. 3.

Preferably, the rice specific expression promoter is extracted from *Oryza sativa* L cv Nipponbare.

The promoter shown in SEQ ID No. 1 is a named as promoter POsRo5, and is a root specific expression promoter; the promoter shown in SEQ ID No. 2 is a named as promoter Psubs3, and is promoter expressed when stressed by water logging; and the promoter shown in SEQ ID No. 3 is a named as promoter POssalt2, and is salt-inducible expression which expresses when stressed by salt.

In another aspect, the present invention provides the use of the rice specific expression promoters in breeding of transgenic plants, characterized in that the application includes connecting the rice specific expression promoters to the upstream of the gene sequence to be expressed in the vector to construct recombinant expression vector and transforming the recombinant expression vector into plant cells, tissues or organs for breeding.

Preferably, the promoter is used to improve the plant growth characteristics, and the plant is monocotyledon, such as rice, wheat, corn, barley, sorghum or oat.

On the other hand, the present invention provides a method of increasing the salt-tolerance of plants, characterized in that, the method includes connecting the rice salt-inducible expression promoter POssalt2 (SEQ ID No. 3) to the target gene to construct recombinant vector and importing the recombinant vector into the target plant so that when the salt increases in the environment in which the target plant grows, the rice salt-inducible expression promoter POssalt2 will induce the expression of the target gene, improving the survivability of the plant in saltine environment. On the other hand, the present invention provides the use of the rice specific promoter in regulation of gene specific expression in rice.

Preferably, the gene to be expressed has a character of improving the rice root.

The rice root specific expression promoter POsRo5 is from *Oryza sativa* L cv Nipponbare genome and is a DNA 1485 bp upstream of the transcriptional start site, with SEQ ID No: 1.

The present invention also provides a recombinant expression vector which is recombinant plasmid obtained by inserting the rice root specific expression promoters into the multiple cloning sites of the plant expression vector, and the nucleotide sequence is connected to the upstream of the gene sequence to be expressed in the vector. In an embodiment, the gene to be expressed is GUS gene. The recombinant expression vector is the one obtained by constructing the sequence POsRo5 or the promoter POsRo5 displayed in SEQ ID No. 1 into pCAMBIA1381, called pCAMBIA1381-POsRo5 here. Or the gene to be expressed can be any gene that can improve the rice root tissue. In present invention, the functions of the promoter are identified by the expression of the GUS gene. Preferably, the gene to be expressed is the gene that can improve the character of the rice root tissue.

On the other hand, the present invention provides use of the promoter Psubs3 (SEQ ID No. 2) in breeding of transgenic plants, characterized in that the application includes connecting the promoter Psubs3 to the upstream of the gene sequence to be expressed in the vector to construct recombinant expression vector and transforming the recombinant expression vector into rice cells, tissues or organs for breeding.

Further, the application is used to improve the rice growth properties, particularly to the growth and improvement of the root.

TECHNICAL EFFECT

The present invention is to clone promoters from rice, then perform the functional validation by using transgenic technology, and at the same time, analyze the tissue expression pattern of the gene in rice. The promoter sequences of the present invention are used to substitute the constitutive promoter to drive the specific expression of the target gene in the rice, especially root, increase the transgene effect, avoid unnecessary waste of matter energy, improve the rice root characteristics efficiently, and breed ideal transgenic

BRIEF DESCRIPTION OF THE DRAWINGS

Hereinafter, the embodiments of the present invention are illustrated by taking in conjunction with the accompanying drawings, wherein.

DETAILED DESCRIPTION OF THE EMBODIMENTS

Figure 1:
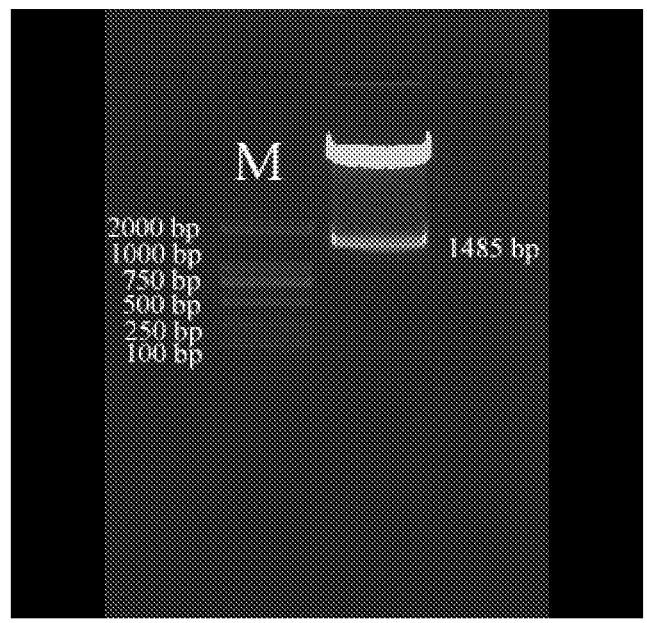
FIG. 1 shows the results of the enzyme digestion validation for the expression vector pCAMBIA1381-POsRo5, according to embodiment 1.
Figure 2:
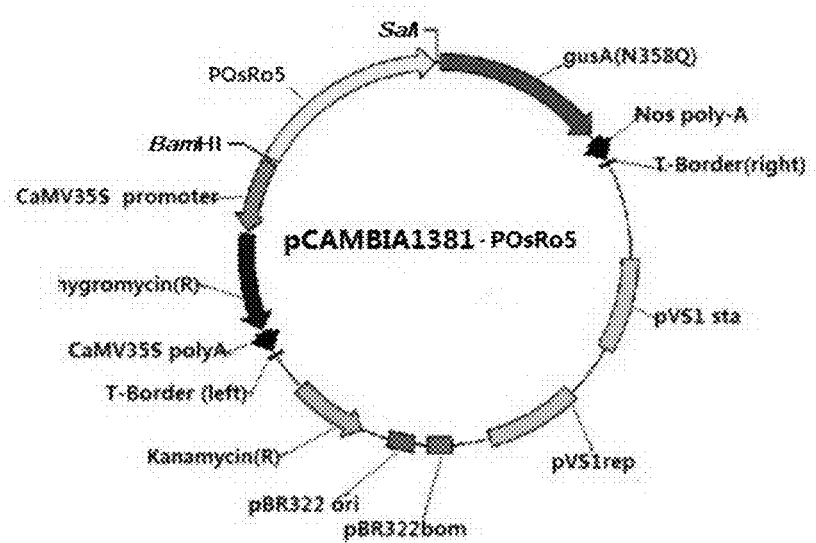
FIG. 2 shows the schematic diagram of the vector pCAMBIA1381-POsRo5, wherein, POsRo5 is on the GUE gene upstream.

The present invention will be apparent from the following detailed description by taking in conjunction with the accompanying drawings and the embodiments, but without limiting the protection scope of the present invention into the scope specified in the embodiments.

Unless otherwise specified, the experimental methods used in the following embodiments are normal methods. The following involved experimental materials are available in the market.

Embodiment 1

Obtaining of Root-Specific Expression Promoter and Construction of Expression Vector (1) Clone of Promoter POsRo5

According to the whole genome sequence of *Oryza sativa* L cv Nipponbare provided by NCBI, the amplification primer is designed by using the primer design software primer5 based on the sequence specified in SEQ ID No. 1, and the restriction site for the primer is designed according to the characteristics of the selected vector and target gene, and the primer sequence is as follows:

FP:
(SEQ ID NO: 4)
GGATCCACCCCCTTAATCAAAAACAACA

RP:
(SEQ ID NO: 5)
GTCGACTTGATGCAAAGGAGCAACGAGC

Wherein, GGATCC base is the recognition site and protective base of the restriction enzyme BamHI, and GTCGAC base is the recognition site and protective base of the restriction enzyme SalI.

Taking the rice genome DNA as a template, use the KOD pfu ultra for PCR amplification. The reaction system (50 μL) is as follows. Perform 1% agarose gel electrophoresis for amplification products.

KOD reaction system (total volume 50 μL) PCR amplification protocol of KOD reaction system

| 10 × KOD buffer | 5 μL | 95° C. 3 min | |
|---|---|---|---|
| MgSO4 | 4 μL | 95° C. 30 s | |
| dNTPs | 5 μL | 58° C. 30 s | 35 cycles |
| Primer (Pf + Pr) | 4 μL | 68° C. 2 min | |
| KOD enzyme | 1 μL | 68° C. 10 min | |
| ddH₂O | 29 μL | 4° C. hold | |
| Template | 2 μL | | |

(2) Adding Ploy A and Linking to T Vector

Recycle the PCR products, and add poly A tail and link to T vector in order to obtain cloning vector.

Add system A: place 3.175 μL recycled product and 1.825 μL A-added mixture (5× Taq buffer 2 μL, 25 mM MgCl2 0.5 μL, 100 mM dATP 0.5 μL, Taq polymerase 0.25 μL) at 72° C. for reaction for 30 min.

Link to T vector: take 4 μL A-added product and 1 μL vector T and place them at 25° C. for reaction for 30 min to obtain the target product, and transfer the product into the *E. coli* competence.

(3) Transform the *Escherichia coli* Competent Cells

① Transfer the solution of the A-added linking T vector into 1.5 mL Eppendorf tube containing 100 μL competent cells, and keep it on the ice for 30 min;

② After heat shock at 42° C. for 90 s, immediately put it in ice bath for 2 min;

③ Add 500 μL LB liquid medium and place it in 37° C. shake incubator for cultivation for 1 h (120 r/min) to make the bacteria recover to the normal growth situation ④ Take 100 μL of the bacteria solution and smear it onto the ampicillin-contained LB screen plate. After the bacteria solution is fully absorbed by the culture medium, place the culture dish upside down for cultivation at 37° C. for 16~24 h. ⑤ Select the clones which are enzyme digestion verified and send to BGI-Beijing for sequencing analysis to obtain the promoters of the candidate genes.

(4) Construction of Promoter Expression Vector

After digestions with corresponding double enzymes, recycle the promoter fragment and the linear processed plasmid pCAMBIA1381. Link the recycled target fragment and linearized vector with T4 ligase (1 μL 10×T4 ligase buffer, 1 μL T4 ligase, 2 μL linearized vector, 6 μL target fragment), PCR and double enzyme digested colony to obtain the expression vectors of the corresponding promoters.

(5). Transform *Agrobacterium tumefaciens* EHA105 with Expression Vector

① Take 10 μL expression vector plasmid DNA and add into the *agrobacterium* competent cells which are taken out of the ultra-low temperature freezer, and mix them and put them into ice bath for 30 min;

② Quickly freeze for 1 min with liquid nitrogen;

③ Add into 1 mL LB culture medium and culture at 28° C. and at speed 120 r/min for 4 h;

④ Centrifuge at speed 4000 r/min for 1 min, and discard the supernatant. Add into 150 μL culture medium for resuspending, and smear the bacteria solution onto the LB solid plate containing 50 μg/mL Kan and 10 μg/mL Rif;

⑤ Culture at 28° C. for 2~3 days until the growth of individual colony, and identify the colony PCR.

⑥ Select the positive clones and store them with 50% glycerin (1:1).

*Agrobacterium*-Mediated Rice Genetic Transformation (1) Callus Induction

Soak the sterilized seeds with 30° C. sterile water in dark for a night, remove the embryos with scalpel, and place them onto the induction medium. Put 12 embryos in each dish (100×25 mm disposable plastic culture dish, containing 50 ml induction medium), and keep the inducing callus at 30° C. in dark for 2~3 weeks until they grow light yellow granular calluses.

(2) Pre-Culture

Select granular calluses without scab from the culture medium and place them onto the new induction medium for culturing at 30° C. in dark for 3~5 d.

(3) Dip Dyeing and Co-Culture

Transfer the pre-cultured calluses into 50 ml sterile tube, add expression vector *agrobacterium* solution and soak for 20 min, pour out the bacteria solution, and sip up the residual bacteria solution with sterile filter paper. Then spread the calluses onto the co-culture medium evenly, and keep them at 23° C. in dark for 2~3 days.

(4) Recovery

Transfer the co-cultured calluses onto the recovery medium (avoid callus overlapping). Culture at 23° C. in dark for 3~5 days.

(5) Screen

Select the brightly colored granular resistant/embryonic calluses in light yellow without bacterial plague from the screening medium, and transplant them in screening medium, 30 pieces in each dish, and culture at 30° C. in dark for 2~3 weeks until they grow new resistant granular calluses.

(6) Differentiation

For each transformation (all calluses reproduced by one callus during screening), select and transfer 3 individual embryonic calluses into a region of the differentiation medium, and culture them in 30° C. lighting incubator (16 h lighting/8 h dark) for 3~4 weeks until they send forth seedlings.

(7) Rooting

Select two strong seedlings from each region and transfer them into the rooting medium, culture them in 30° C. lighting incubator (16 h lighting/8 h dark) for about 3 weeks, and perform the identification and transplant into the field.

Identification of Promoter Expression Characteristics in Transgenic Rice Seedlings GUS can react with the chromogenic substrate X-gluc and appears blue, so the GUS expression level and expression pattern can be researched qualitatively by histochemical staining.

For the reagent for GUS staining and the procedures, refer to the method proposed by Jefferson (Jefferson R A et al. GUS fusion: β-Glucuronidase as a sensitive and versatile gene fusion marker in higher plant[J]. EMBO J., 1987, 6:3901-3907), as follows:

① Staining: Soak the samples to be tested into GUS dye liquor, and place in 37° C. incubator for 24 h-36 h.

② Destaining: Add 100% ethyl alcohol and soak until they are destained completely. They can be stored with solution containing 30% glycerin and 70% ethyl alcohol.

③ Take photos and record under the microscope.

Figure 3:
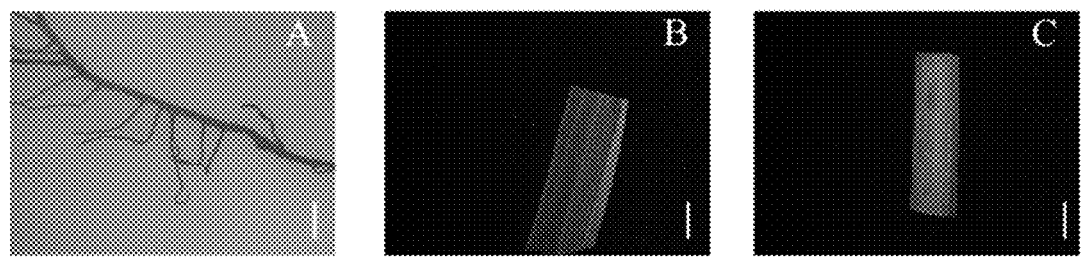
FIG. 3 shows the results of GUS staining for the obtained POsRo5: GUS positive transgenic rice plant, wherein A, B and C represents the root, leaf and stem of the seedling.

The results of the GUS staining by the above method are as shown in FIG. 3 (scale=0.2 cm), wherein, for the POsRo5: GUS transgenic rice plants, in the seedling period, the promoters are only expressed in the root (A) but not dyed in the leaf (B) or stem (C). This suggests that the promoter POsRo5 driving GUS gene is only expressed in the root, and that the promoter POsRo5 is root-specific expression promoter.

Embodiment 2

This embodiment provides a promoter that is significant to the growth of the rice root and is responsive to the external water environment expression.

Step 1. Cloning of Promoter Psubs3 and Construction of Vector pCAMBIA1381-Psubs3

According to the whole genome sequence of *Oryza sativa* L cv Nipponbare provided by NCBI, design the amplification primer based on the sequence specified in SEQ ID No. 2, and design the restriction enzyme cutting site of the primer according to the characteristics of the selected vector and target gene. The primer for amplification includes:

```
Forward Primer: EcoRI
                                       (SEQ ID NO: 6)
GAATTCTTTACTCACCGTGTCCTCTGTT Forward Primer: HindIII
                                       (SEQ ID NO: 7)
AAGCTTTGTATCTCTCTCTGGTAGTTAG
```

Taking the rice variety *Oryza sativa* L cv Nipponbare as the template, by utilizing the forward primer and the reverse primer to amplify the promoter Psubs3, and by the conventional PCR system, uses the following amplification protocol:

Pre-denaturation at 95° C. for 5 min; Denturation at 95° C. for 30 s; Annealing at 58° C. for 30 s; Elongation at 72° C. for 2 min and 30 s; executing 35 cycles from pre-denaturation at 95° C. to elongation at 72° C.; At last elongation at 72° C. for 10 min.

Recycle the PCR amplified target fragment, and the target fragment is 1939 bp. Link it to PGEM-T-Easy vector (purchased from Promega, blend in the proportion as specified in the vector manual), and send it to Invitrogen (a company which can do the sequencing) for sequencing, wherein the nucleotide sequence is as shown in SEQ ID No: 2.

Figure 4:
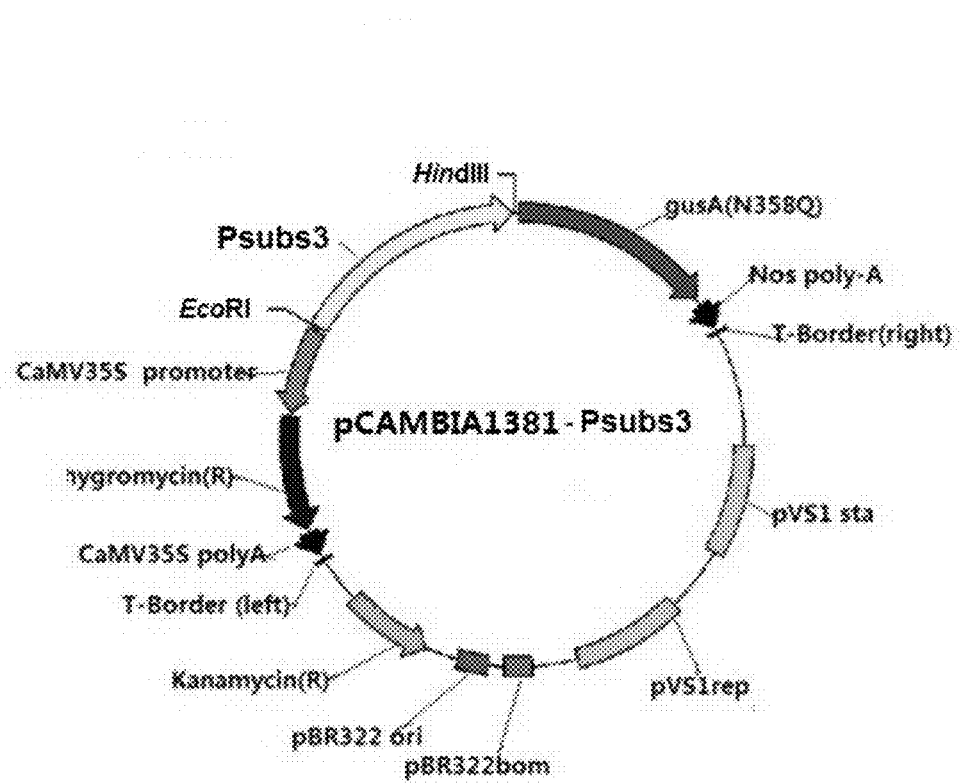
FIG. 4 shows the schematic diagram of Psubs3 promoter constructed in carrier vector pCAMBIA1381, according to embodiment 2.

Perform double enzyme digestion for the PGEM-T-Easy vector which is linked with Psubs3 by using HindIII and EcoRI, recycle the promoter Psubs3 fragment. Simultaneously, perform linear processing to pCAMBIA1381 by using HindIII and EcoRI, link the Psubs3 fragment topCAM-BIA1381 vector to obtain the plant expression vector pCAMBIA1381-Psubs3 gintegratin Psubs3 and GUS gene, as shown in FIG. 4. Transfer the plant expression vector pCAMBIA1381-Psubs3 into the *Agrobacterium tumefaciens* (*Agrobacterium tumefaciens*) EHA105 by utilizing freeze-thaw method.

Step 2: *Agrobacterium*-Mediated Rice Genetic Transformation

Remove the glumes of the mature seeds, and soak them with 70% ethyl alcohol for 1 min, and discard the ethyl alcohol. Soak the seeds in 50% sodium hypochlorite (the concentration of available chlorine in the original solution is bigger than 4%) solution containing 1 drop of Tween 20 for 40 min (at 150 r/min). Discard the sodium hypochlorite and wash the seeds with sterile water for 5 times until the solution is clean and free of flavor of sodium hypochlorite. Soak the seeds in sterile water for a night. Remove the embryo along with the seed's aleurone layer with scalpel, and transplant the embryo onto the callus induction medium. After dark culture at 30° C. for 11 days, separate the callus from the endosperm and germ, pre-culture the degerminated primary calluses in good condition and with strong division for 3~5 days before using for *agrobacterium* transformation.

Perform *agrobacterium*-mediated genetic transformation for the *Agrobacterium tumefaciens* in which the pCAMBIA1381-Psubs3 recombinant expression vector is transferred, and for the genetic transformation, transformant selection and transgenic plants regeneration, refer to the method proposed by Yongbo Duan (Yongbo Duan, Chenguang Zhai, et al. An efficient and high-throughput protocol for *Agrobacterium* mediated transformation based on phosphomannose isomerase positive selection in *Japonica* rice (*Oryza sativa* L.)[J]. Plant Cell Report, 2012.DOI 10.1007/s00299-012-1275-3).

Total 32 plants are obtained. Extract the DNAs from the plants, and after PCR identification, 28 positive pCAMBIA1381-Psubs3 plants are obtained.

Step 3. Psubs3 Promoter Activity Identification

Referring to the method proposed by Jefferson (Jefferson R A et al. GUS fusion: β-Glucuronidase as a sensitive and versatile gene fusion marker in higher plant[J]. EMBO J., 1987, 6:3901-3907), evacuate the tissue to be dyed, and soak it into the dyeing liquor and dye it at 37° C. for 24 h. When destaining, process it with 95% ethyl alcohol at 37° C. until the negative control material turns white.

Figure 5:
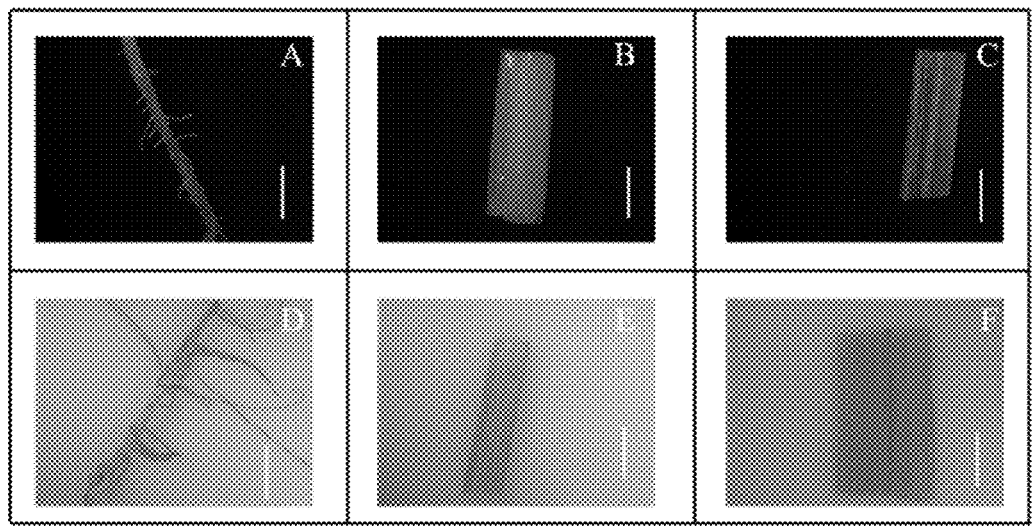
FIG. 5 shows the schematic diagram of the Gus staining results, according to embodiment 2.

Dye the positive Transgenic plant tissue 21 days after the seed germination. For the rice plants growing under normal conditions, after 24 h dyeing, the root (A), the stem (B), and the leaf (C) are free of GUS activity, but for the ones submerged in water for 1 hour and being dyed for 24 h, there are strong GUS expression (scale=5 mm) in the root (A), the stem (B), and the leaf (C). For the results, see FIG. 5.

Extract the RNAs of the 14-day seedlings before and after being submerged in water, and obtain cDNAs by inverse transcription. Detect the GUS gene expression level by real-time fluorogenic quantitative PCR, and simultaneously, compare with the rice house-keeping gene ACTIN as control. The changes in the GUS gene expression reflect the water-induced activity of Psubs3 promoter.

The RT-qPCR is SuperReal fluorogenic quantitative Pre-Mix Plus (TIANGEN, SYBR Green, FP205) from TIANGEN (Beijing). Taking the rice ACTINgene as the reference gene to quantitate the applied RNA templates. Process the obtained signals and data by using $2^{-\Delta\Delta CT}$ ($\Delta CT=CT$ target gene−CT reference gene; $\Delta\Delta CT=\Delta CT$ pose-processing−$\Delta CT$ control). Repeat three times for each gene. The quantitative primer used in this experiment is: Actin-FP 5'-CCTGACGGAGCGTGGTTAC-3' (SEQ ID NO: 8); and Actin-RP, 5'-CCAGGGCGATGTAGGAAAGC-3' (SEQ ID NO: 9) for ACTIN amplification; Gus-FP, 5'-TACGGCAAAGTGTGGGTCAATAATCA-3' (SEQ ID NO: 10)

Figure 6:
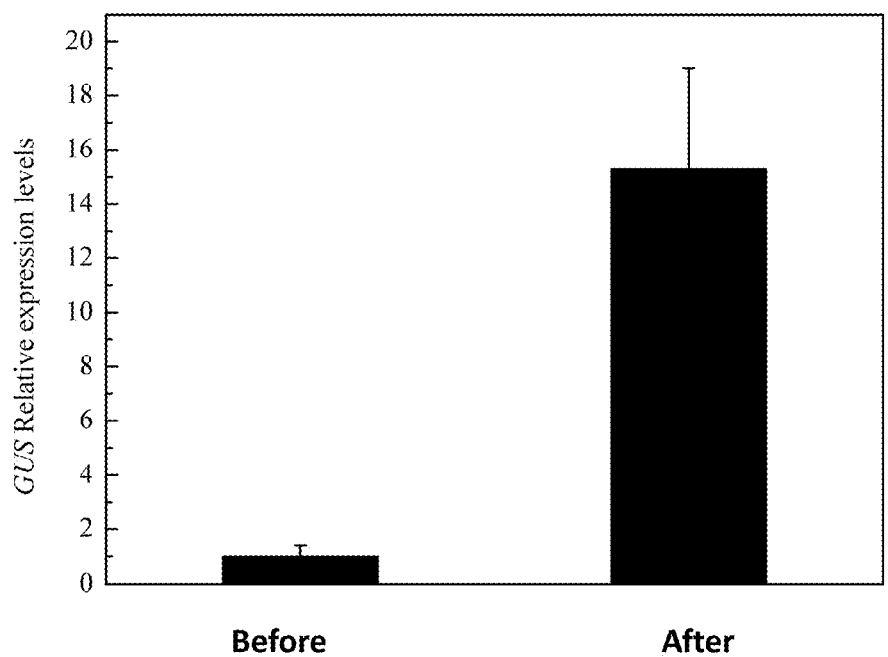
FIG. 6 shows the comparison between before and after submerging the rice plants in water.

And Gus-RP, 5'-CAGGTGTTCGGCGTGGTGTAGAG-3' (SEQ ID NO: 11) for GUS amplification. The results as shown in FIG. 6 suggest that, the GUS gene expression level in the transgenic plants after being submerged in water is 15.3 times of the transgenic plants not being submerged in water, therefore, it suggests that the Psubs3 promoter has relatively strong water-inducible activity.

Embodiment 3

Figure 7:
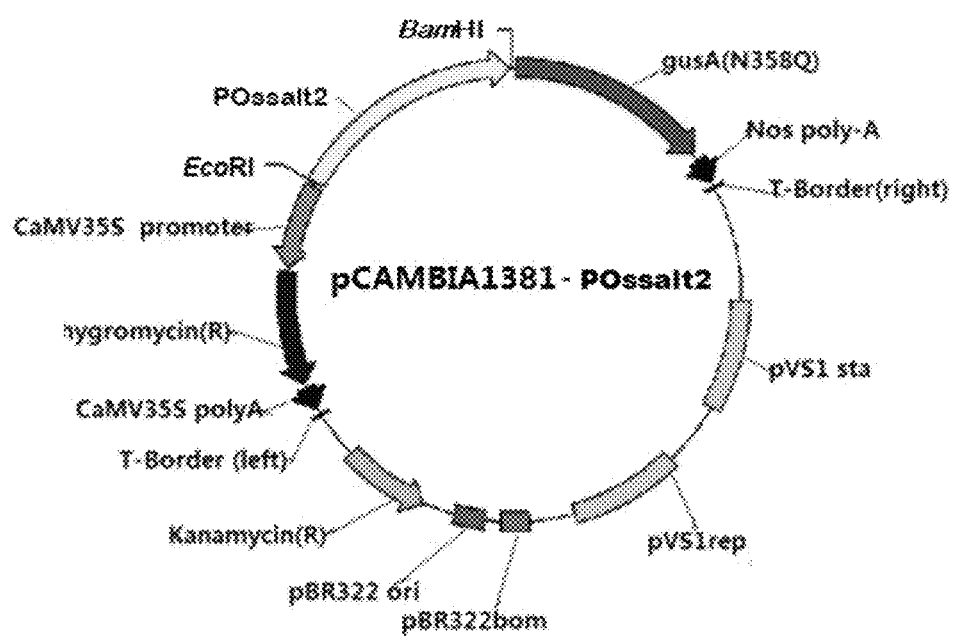
FIG. 7 shows the constructed expression carrier vector pCAMBIA1381-POssalt2, utilizing the promoter POssalt2 to drive the downstream GUS gene expression, according to embodiment 3.
Figure 8:
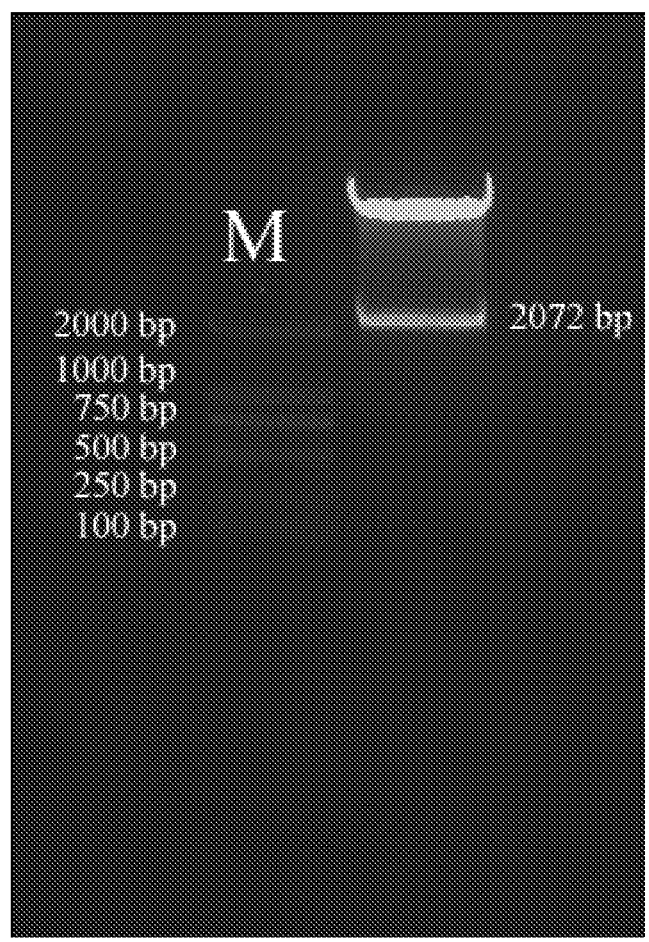
FIG. 8 shows the results of the enzyme digestion validation for the expression vector pCAMBIA1381-POssalt2, according to embodiment 3.

1. Obtaining of POssalt2 Promoter Containing Restriction Enzyme Cutting Site
(1) Primer Design It is in accordance with the whole genome sequence of *Oryza sativa* L cv Nipponbare provided by NCBI. Design the amplification primer based on the sequence specified in SEQ ID No. 3, and design the restriction enzyme cutting site according to the characteristics of the selected vector and target gene In this embodiment, taking the rice binary expression vector (FIG. 7, from pCAMBIA, the publically used vector stored by Rice Team, GMOs and Derived Products Inspection and Supervision Center, Ministry of Agriculture, P. R. China) pCAMBIA1381 for example, the target gene is GUS gene, and the specifically designed primer sequence is as follows, wherein the italic base is the restriction enzyme cutting site:

```
Forward primer:
                                     (SEQ ID NO: 12)
GAATTCAATCTCTACTACTTAAATTCCAEcoRI Reverse primer:
                                     (SEQ ID NO: 13)
GGATCCCCAAATCAGCTAACCCGCGCCTBamHI
```

(2) Cloning of Promoter and Construction of Expression Vector

Taking the rice genome DNA as the template, use the KOD pfu ultra for PCR amplification. Perform 1% agarose gel electrophoresis for amplification products. Recycle the PCR products, and add polyA tail and link to T vector in order to obtain cloning vector. Send the cloning vector to BGI-Beijing for sequencing analysis to obtain the promoter POssalt2 in length of 2072 bp.

Respectively digest the promoter POssalt2 with corresponding enzyme and linearly process the pCAMBIA1381 plasmid. Perform the linking with T4 ligase to obtain the corresponding pCAMBIA1381-POssalt2 expression vector.
(3). Transform *Agrobacterium Tumefaciens* EHA105 with Expression Vector ① Take and add 10 μL expression vector plasmid DNA into the *agrobacterium* competent cells taken out from the ultra-low temperature freezer, and mix them and put them into ice bath for 30 min;
② Quickly freeze for 1 min with liquid nitrogen;
③ Add into 1 mL LB culture medium and culture at 28° C. and at speed 120 r/min for 4 h;
④ Centrifuge at speed 4000 r/min for 1 min, and discard the supernatant. Add into 150 μL culture medium for resuspending, and smear the bacteria solution onto the LB solid plate containing 50 μg/mL Kan and 10 μg/mL Rif;

⑤ Culture at 28° C. for 2~3 days until the growth of individual colony, and identify the colony PCR.
⑥ Select the positive clones and store them with 50% glycerin (1:1).

2. Obtaining Transgenic Plants
(1) Rice Genetic Transformation
① Callus Induction Soak the sterilized rice seeds with 30° C. sterile water in dark for a night, remove the embryos with scalpel, and place them onto the induction medium. Put 12 embryos in each dish (100×25 mm disposable plastic culture dish, containing 50 ml induction medium), and keep the inducing callus at 30° C. in dark for 2~3 weeks until they grow light yellow granular calluses.

② (2) Pre-Culture

Select granular calluses from the culture medium and place them onto the new induction medium for culturing at 30° C. in dark for 3~5 days.

③ Dip Dyeing and Co-Culture

Transfer the pre-cultured calluses into 50 ml sterile tube, add *agrobacterium* solution (OD600=0.2) and soak for 20 min, pour out the bacteria solution, and sip up the residual bacteria solution with sterile filter paper. Then spread the calluses onto the co-culture medium evenly, and keep them at 23° C. in dark for 2~3 days.

④ Recovery:

Transfer the co-cultured calluses onto the recovery medium for culturing at 30° C. in dark for 3~5 d.

⑤ Screen:

Select the brightly colored granular embryonic calluses in light yellow without bacterial plague from the screening medium, and transplant them in screening medium, 30 pieces in each dish, and culture at 30° C. in dark for 2~3 weeks until they grow new resistant granular calluses.

⑥ Differentiation:

For each transformation, select and transfer 3 individual embryonic calluses into a region of the differentiation medium, and culture them in 30° C. lighting incubator (16 h lighting/8 h dark) for 3~4 weeks until they send forth seedlings.

⑦ Rooting:

Select two strong seedlings from each region and transfer them into the rooting medium, culture them in 30° C. lighting incubator (16 h lighting/8 h dark) for about 3 weeks, and perform the identification and transplant into the field.

(2) Identification of Transgenic Plants

Totally, 33 pCAMBIA1381-POssalt2 plants (POssalt2: GUS Transgenic rice plants) are obtained. Extract the DNAs of the Transgenic plants by conventional method, and test the transformed plants by amplifying the hygromycin gene with PCR, and 30 positive plants are obtained.

3. Promoter Activity Identification
(1) GUS Tissue Histochemical Staining

Referring to the method proposed by Jefferson et al, perform GUS staining analysis for the plants which are tested positive before and after being processed with 200M NaCl solution. Soak the samples to be tested into the GUS dyeing solution, and keep it in 37° C. incubator for 24 h. Then immerse the samples in 100% ethyl alcohol until they are destained completely, and take photos.

Figure 9:
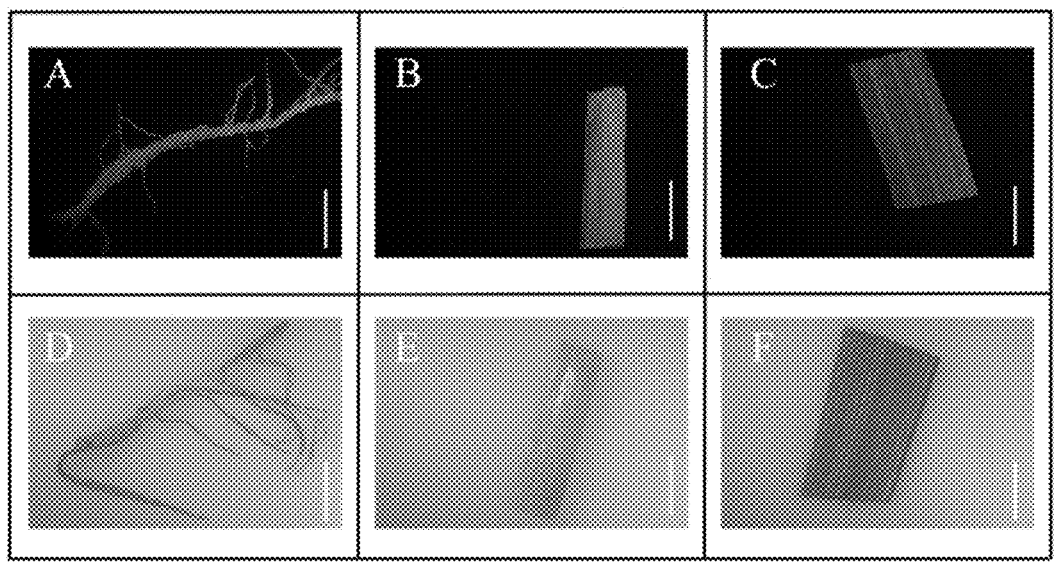
FIG. 9 shows the analysis of POssalt2 activity by GUS staining, wherein A, B and C respectively represent the staining result of the root, stem and leaf of the transgenic plant 10 days before processing with 200 mM NaCl, and D, E and F respectively represent the root, stem and leaf staining results after being processed with 200 mM NaCl, according to embodiment 3.

The staining results are as shown in FIG. 9. The root (A), the stem (B) and the leaf (C) of the Transgenic plants not processed with 200 mM NaCl solution are not apparently colored. But after being processed with 200 mM NaCl solution, the root (D), the stem (E) and the leaf (F) of the Transgenic plants have deep blue. This suggests that, after being processed with salt, the salt-inducible promoter can activate the expression of the GUS genes, and this proves that the promoter is a salt-inducible expression promoter and without background expression.

(2) Quantitative PCR Analyzing the Promoter Activity

The GUS staining results qualitatively suggests that, POssalt2 is a salt-inducible expression promoter. To validate the activity of salt-inducing strength POssalt2, we extracted the RNAs of the Transgenic seedlings 10 days before and after being induced by 200 mM NaCl solution, and inversely transcribed them to cDNAs, and tested the changes in expression of GUS genes driven by POssalt2 before and after being induced by 200 mM NaCl solution by using fluorogenic quantitative PCR (RT-qPCR) method.

Apply RNAprep pure Kit (for plant) (TIANGEN, Spin Column, DP432) from Tiangen Biotech (Beijing) Company. Perform inverse transcription for the obtained RNA by the following procedures: Add 5 μL RNase-Free ddH$_2$O, 2 μL 5×gDNA buffer, 3 μL RNA into the RNase-free centrifuge tube, and place at 42° C. to incubate for 3 min, and place the tube on ice; Successively add 5 μL RNase-Free ddH$_2$O, 2 μL FQ-RT Primer Mix, 2 LL 10× Fast RT Buffer, and 1 μL RT Enzyme Mix into the above reaction liquid and mix them thoroughly, then place the mixture at 42° C. to incubate for 3 min and place on ice, and cDNA is obtained.

The RT-qPCR is SuperReal fluorogenic quantitative Pre-Mix Plus (TIANGEN, SYBR Green, FP205) from TIANGEN (Beijing). Taking the rice ACTIN gene as the reference gene to quantitate the applied RNA templates. Process the obtained signals and data by using $2^{-\Delta\Delta CT}$ ($\Delta CT=CT$ target gene–CT reference gene; $\Delta\Delta CT=\Delta CT$ pose-processing–$\Delta CT$ control). Repeat three times for each gene. The quantitative primer used in this experiment is: Actin-FP 5'-CCTGACGGAGCGTGGTTAC-3' (SEQ ID NO: 8); and Actin-RP, 5'-CCAGGGCGATGTAGGAAAGC-3' (SEQ ID NO: 9) for ACTIN amplification; Gus-FP, 5'-TACGGCAAAGTGTGGGTCAATAATCA-3' (SEQ ID NO: 10) And Gus-RP, 5'-CAGGTGTTCGGCGTGGTGTAGAG-3' (SEQ ID NO: 11) for GUS amplification.

Figure 10:
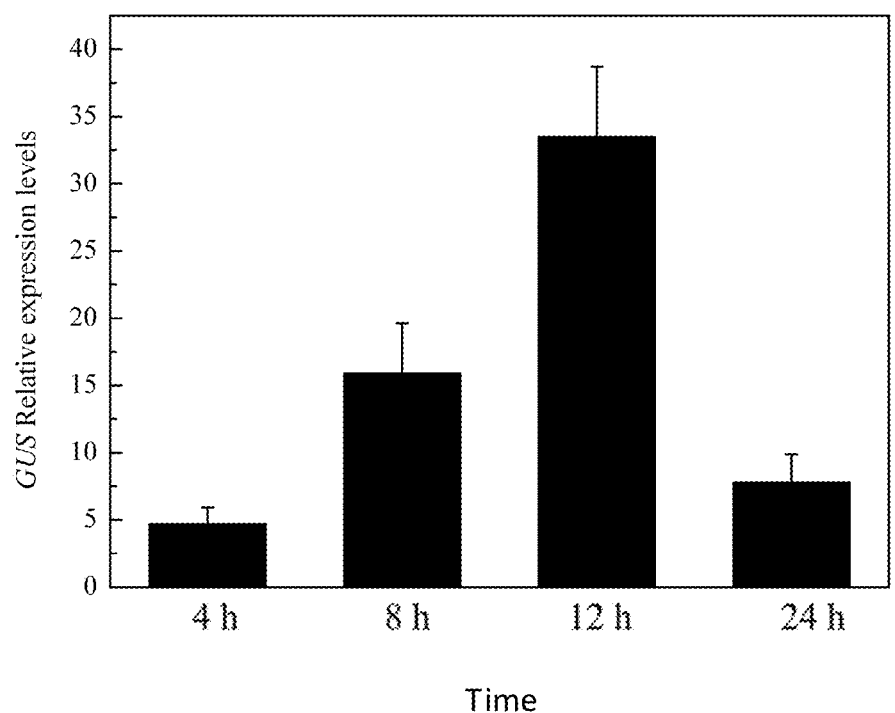
FIG. 10 shows the fluorogenic quantitative PCR analysis for changes in activity of salt-induced POssalt2 promoter, i.e., the GUS gene expression levels separately at 4 h, 8 h, 12 h and 24 h of the 10-day transgenic plant driven by the promoter POssalt2, according to embodiment 3.

The quantitative PCR results are as shown in FIG. 10 that, taking the GUS gene expression level of the 10-day Transgenic seedlings not processed with 200 mM NaCl solution, respectively detect the changes in GUS gene expression levels of the Transgenic plants being processed with 200 mM NaCl solution for 4 h, 8 h, 12 h and 24 h. When the processing time is extended from 4 h to 12 h, comparing non-processed ones, the promoter-activated GUS gene expression level is increased from 4.7 times to 33.5 times, subsequently, when the processing time is up to 24 h, the activity decreased to 7.8 times. This suggests that, POssalt2 promoter is a salt-inducible expression promoter, and the activity after being induced is dozens of times of that before being induced, and the induced activity is up to the peak at 12 h. And this suggests that, POssalt2 is a salt-inducible expression promoter with high activity but without background expression.

What is claimed:

1. A method of using a stress-inducible promoter, wherein said stress-inducible promoter consists of SEQ ID NO:1 or SEQ ID NO:3, wherein the method comprises:
   linking said stress-inducible promoter upstream of a coding region to be expressed in a vector to construct a recombinant expression vector; and
   importing said recombinant expression vector to a rice cell for cultivation.

2. A method of increasing the salt-tolerance of a rice plant, said method comprising connecting SEQ ID NO: 3 to a target coding region to be expressed to construct a recombinant vector; and importing the recombinant vector into a rice plant so that when the salt content in the environment in which the rice plant grows increases, the rice salt-inducible expression promoter of SEQ ID NO: 3 will induce expression of said target coding region.

\* \* \* \* \*